United States Patent [19]

Van Deusen et al.

[11] Patent Number: 5,132,097
[45] Date of Patent: Jul. 21, 1992

[54] APPARATUS FOR ANALYSIS OF SPECIFIC BINDING COMPLEXES

[75] Inventors: Richard A. Van Deusen; Jack J. Lyon; Thomas D. Hillson, all of Ames, Iowa

[73] Assignee: G.D. Research, Ames, Iowa

[21] Appl. No.: 577,802

[22] Filed: Sep. 4, 1990

Related U.S. Application Data

[63] Continuation of Ser. No. 484,439, Feb. 20, 1990, abandoned, which is a continuation of Ser. No. 342,715, Apr. 24, 1989, abandoned, which is a continuation of Ser. No. 13,637, Feb. 11, 1987, abandoned.

[51] Int. Cl.⁵ .......................................... G01N 33/543
[52] U.S. Cl. ................................ 422/82.09; 356/434; 422/82.05; 436/518
[58] Field of Search ............... 422/68.1, 82.05, 82.06, 422/82.07, 82.11, 82.09; 436/518, 164, 172; 356/434, 443, 448

[56] References Cited

U.S. PATENT DOCUMENTS

| | | | |
|---|---|---|---|
| 4,486,536 | 12/1984 | Baker | 422/56 X |
| 4,509,859 | 4/1985 | Markart et al. | 422/82.05 |
| 4,558,013 | 12/1985 | Marinkovich | 422/56 X |
| 4,578,358 | 3/1986 | Oksman | 422/56 X |
| 4,592,893 | 6/1986 | Poppe | 422/56 |
| 4,737,464 | 4/1988 | McConnell et al. | 422/82.05 |

Primary Examiner—Jill A. Johnston
Attorney, Agent, or Firm—Kinney & Lange

[57] ABSTRACT

A system for analysis of specific binding complexes. A reaction surface is treated with a specific receptor chemical (SRC) having specific binding properties and is allowed to bind with an unknown reactant to form specific binding complexes (SRC) on the reaction surface. The output of a laser is directed through the reaction surface to a detection mechanism. Shadows in the detected light may be interpreted to detect the presence of the unknown reactant. The unknown reactant may also be quantified. Preferred embodiments of apparatus, and methods of their use, are disclosed for detecting the presence of the unknown reactant within a system for interpreting the results, including interactive system components by which the bases for interpretation may be updated.

2 Claims, 4 Drawing Sheets

APPARATUS FOR ANALYSIS OF SPECIFIC BINDING COMPLEXES

This is a continuation of application Ser. No. 07/484,439, filed Feb. 20, 1990 which is a continuation of application Ser. No. 07/342,715, filed apr. 24, 1989, which is turn is a continuation of application Ser. No. 07/013,637, filed Feb. 11, 1987, all of which are now abandoned.

BACKGROUND OF THE INVENTION

1. Field of the Invention.

The present invention relates to an apparatus and method for qualitative and/or quantitative analysis of a specific binding complex and to a system for interpreting the shadows created on a detector by light passing through the specific binding complex.

2. Description of the Prior Art.

biological systems involve the specific binding of two independent reactants to form a specific binding complex (SBC). These reactants have been the basis of assay systems which attempt to determine the presence of the unknown reactant by using a known amount of a specific receptor chemical (SRC) in a variety of configurations. Most of these assays are based on labeling the SRC with detectable substances such as radioisotopes, enzymes, fluorochromes and the like. The labeled SRC is detected, for example, by use of a scintillation counter after the radioactively labeled SRC and the unknown reactant have been allowed to form the SBC.

Typical of the described assays are immunoassays, which employ a labeled specific antibody to detect the presence of its antigen and, in some cases, quantify the amount of antigen present in the test sample. Examples of such assays are found in Zuk and Ullman U.S. Pat. No. 4,256,834 and Hornby et.al. U.S. Pat. No. 4,238,565 as well as in Weir, *Handbook of Experimental Immunology*, 3rd ed., Blackwell Scientific Publications, Philadelphia, PA.

In these prior art systems, the formation of the SBC and its detection are accomplished on a glass or plastic surface, or in a container. After the SBC is formed, the net reaction in the system is measured. The problem encountered in such prior art systems is that the reactants need to come to equilibrium (which usually takes 30 to 120 minutes) to form a sufficient number of SBCs for detection by the system. After equilibration, the level of the SBCs formed during the reaction is estimated by measuring the quantity of labeled SRC bound to the unknown reactant on the solid phase or in the container. The value obtained is then compared to a standard or independent control test to determine if a particular reactant is present and, in some cases, to provide an estimate of the unknown reactant's concentration.

Biological reagents are inherently variable. Therefore, values obtained from experimental controls will vary from reagent lot to reagent lot, and from test to test with the same lot of reagents. This variation can lead to large differences in result interpretation with respect to the amount of unknown reactant in any one test. Also, the prior art systems require the independent assay of standard(s) or control samples since they cannot be incorporated with the method or apparatus. Use of standardized reagents reduces the variation between the unknown reactant assay and the independently run control assay. However, the reduction is not sufficient to provide the type of accurate assay results that are presently needed.

Some prior art systems employ lasers in the detection of products of a specific binding reaction by concentrating on the detection of the total label bound at equilibrium, or a change in some related factor after the reaction has come to equilibrium. For example, Uzgiris U.S. Pat. No. 4,171,956 discloses a method wherein a sample is vaporized, a laser exciting a fluorescent molecule bound to one of the specific reactants in the vaporized test sample. Light is emitted by the fluorescent molecule. Another example is that described in Noeller U.S. Pat. No. 4,419,483 wherein polarized laser light stimulates the fluorescent label attached to one of the specific reactants in the reaction mixture. The difference between the level of polarized fluorescent light emitted by the fluorescent label bound in the reaction and the free fluorescent label in solution is then measured.

Hirschfeld U.S. Pat. No. 4,447,546 describes a fluorescent immunoassay apparatus and method for detection of an antigen-antibody complex. Hirschfeld employs a capillary tube with one of the reactants bound to its surface. A fluorescent label on another of the specific reactants is excited by radiation from an axially disposed optical fiber within a capillary tube only if it has bound to the reactant on the surface of the capillary tube. Other similar methods are described in Carter et.al. U.S. Pat. No. 4,508,532 and Lundstrom et.al. U.S. Pat. No. 4,521,522 which show methods for measuring the effects of specific binding reactants on elliptical polarization or refraction of a source light.

In Takekawa Pat. No. 4,452,759, a light blocking system is used to measure an agglutination pattern of blood corpuscles. The light blocking system measures the presence, absence or degree of agglutination by a measurement of the total amount of light blocked. The system of the Takekawa Patent, however, would only be suitable for assay systems where agglutination or precipitation reactions occur, and would not be suitable for accurate quantitative measurements of individual specific binding complexes.

Morris et.al. U.S. Pat. No. 3,905,767 includes a process for qualitative or quantitative analysis of antigens or antibodies by using a light source, a reflective surface and a light sensor for sensing scattered light. The antigen and antibody molecules react in a gel on the reflective surface to form a precipitate. The extent to which the light beam is scattered by the precipitate is measured. Because of the requirement for the formation of a precipitate, the Morris et.al. process produces only an estimate of the total SBCs in a sample, and has limited application.

SUMMARY OF THE INVENTION

The present invention relates to a system for detecting an unknown reactant, such as an enzyme, an enzyme substrate, an antibody or an antigen. A test strip is employed and has a reactive surface which is coated with a known specific receptor chemical (SRC) with specific binding characteristics. The SRC has specific binding affinity for the unknown reactant to form a specific binding complex (SBC) on the reactive surface.

The output from a laser is directed through the reactive surface and the resulting light pattern is detected by a detector assembly. The detected light pattern may be interpreted such that the presence of the SBC is recognized and quantified. In a preferred embodiment, the laser detector assembly includes a fiber optic bundle positioned to collect light transmitted through the reactive surface and a light sensitive semiconductor array at the terminus of the fiber optic bundle. A scanning relative movement between the test strip and the detector assembly allows an analysis of the entire reactive surface, or at least a substantial portion thereof.

Preferably, standard and control SBCs are included on a test strip surface in an area adjacent to, or interspersed between, test areas formed on the reactive surface. The standard and control areas may be scanned in the same manner as the test areas (by the same detector assembly) to provide a measurement of both the standard and control SBCs and the test SBCs. The standard and control SBCs may then be compared to the test SBCs that are formed with the unknown reagent to allow the calculation of an accurate, quantitative value of the amount or concentration of the unknown reactant. It should be noted that equilibration is not a requirement for the measurements and comparisons described herein. This greatly reduces the time required for analysis.

As is indicated above, the values provided by the system of the present invention may be employed to detect and quantify specific unknowns. Additionally, the values from the control tests may be compared with expected values as a check on the condition of the reagents employed in the test, including the reagents in the test areas, as well as to determine whether the test has been properly run. Expected values may be recorded on a carrier which combines the test, standard and control areas and may be employed for various system checks and to gather historic and/or epidemiologic information. Local processors may also be networked for information gathering and dissemination, preferably through a central processor system.

DETAILED DESCRIPTION OF THE PREFERRED EMBODIMENTS

Figure 1:
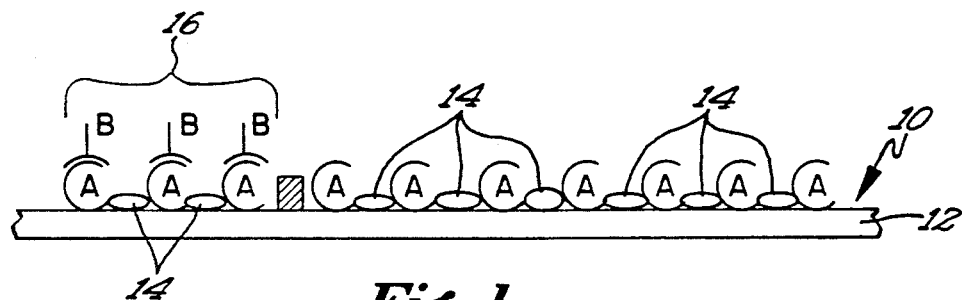
FIGS. 1-3 illustrate the formation of the specific binding complex (SBC) in accordance with the present invention.

Referring to FIG. 1, a layer of a known reactant A is placed on a surface 10 of a strip 12. The known reactant A is bonded to the surface 10 through a specific chemical crosslinking, such as described in Erlanger, B. F., "The Preparation of Antigenic Haptencarrier Conjugates: A Survey, *Methods in Enymol.*", Vol. 70, pp. 85-106, 1980, or through simple adsorption of the known reactant A to the surface 10, such as described in Cantarero, L. A. et.al., "The Adsorptive Characteristics of Proteins for Polystyrene and Their Significance in Solid-Phase Immunoassays," *Anal. Biochem.*, Vol. 105, pp. 375-382, 1980. The strip 12 is then treated with an agent, such as gelatin (See, Kato, K. et.al., "Use of Gelatin to Remove Interference by Serum with the Solid Phase Enzyme Linked Sandwich Immunoassay of Insulin", *FEBS Letters*, Vol. 99, pp. 172-174, 179) or appropriate blocking agents 14 to reduce nonspecific binding of other reagents to the surface 10 of the strip 12. Surface 10 is referred to herein as a "reaction surface". Strips having a "reaction surface", such as strip 12, are referred to herein as "test strips".

One area of the test strip, indicated by bracket 16 in FIG. 1, contains a known amount of a second reactant B bound to the first reactant A. The reactant B is the reactant whose presence and concentration is of interest. As will become apparent from the following discussion, the area 16 (containing the known amount of reactant B bound to reactant A) may be used as a standard or control area in determining the relative amount of reactant B in a test sample applied to the test strip 12. That portion of reaction surface 10 not containing reactant B in FIG. 1, and corresponding areas of test strips in accordance with the present invention are referred to herein as "test areas".

Figure 2:
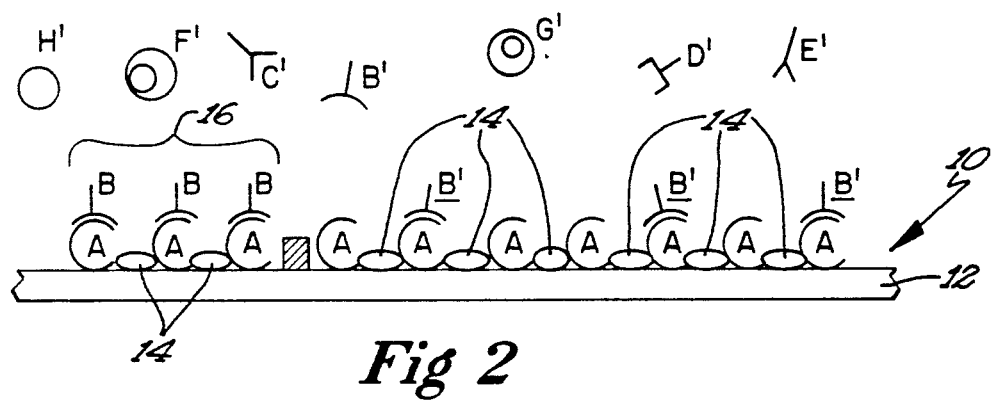

FIG. 2 represents the test strip 12 placed in a test solution containing the test sample which is to be assayed for the presence and concentration of the reactant B'. Reactants B and B' differ only in their origin with the prime indicating a reactant originating in the test sample. The solution may be serum, urine, tissue homogenate or the like with the test strip 12 being placed within the solution for a specified length of time. Since the reactant A is specific only for the reactant B' of the test sample, only the reactant B' will bind to the test strip surface. The test strip 12 is then washed to remove any unbound reactants.

Figure 3:
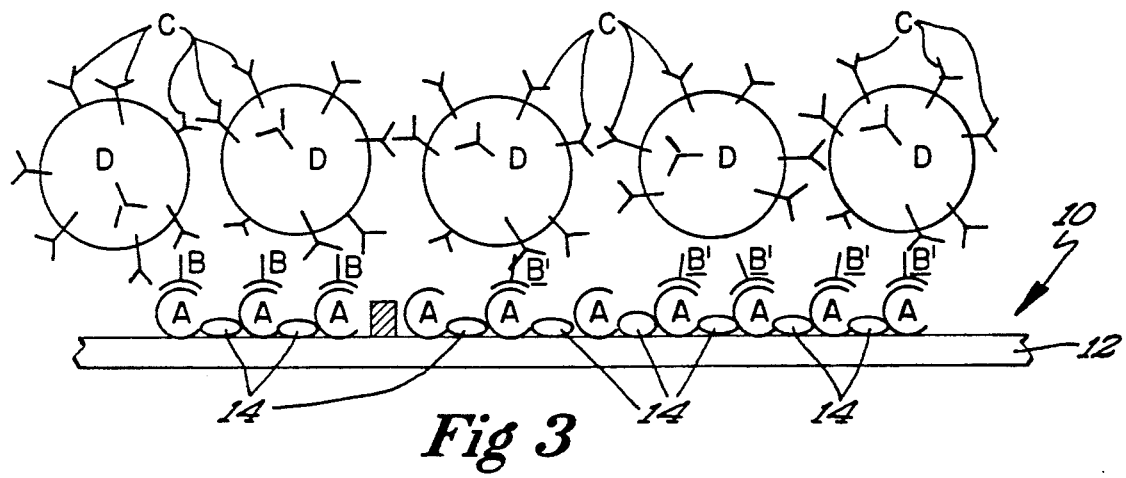

As illustrated in FIG. 3, the test strip 12 is then placed in a solution containing an identifier such as a monoclonal or polyclonal antibody designated by C, which is specific to the reactant B and B'. Preferably, the identifier C is bound to a microbead, such as a polystyrene bead in an approximate diameter range of 0.1 to 1.0 microns, or a globular structure, such as a protein or carbohydrate structure in the approximate range of 0.1 to 1.0 microns, either being represented by the structure designated D in FIG. 3. The antibody C with structure D binds to both reactants B and B' on the test strip 12. The test strip 12 is again washed to remove excess identifier solution. In this manner, a standard or control area and a test area having reactant B or B', respectively, thereon are produced on the same test strip 12. Also, it is not necessary for the reactants to come to equilibrium. Instead, a time base may be established for the allowed reaction time for SBC formation on a test area (see FIG. 2) to which the number of SBC's and standard or control area may be compared. The identifier reaction time (FIG. 3) on all areas is inherently the same.

Figure 4:
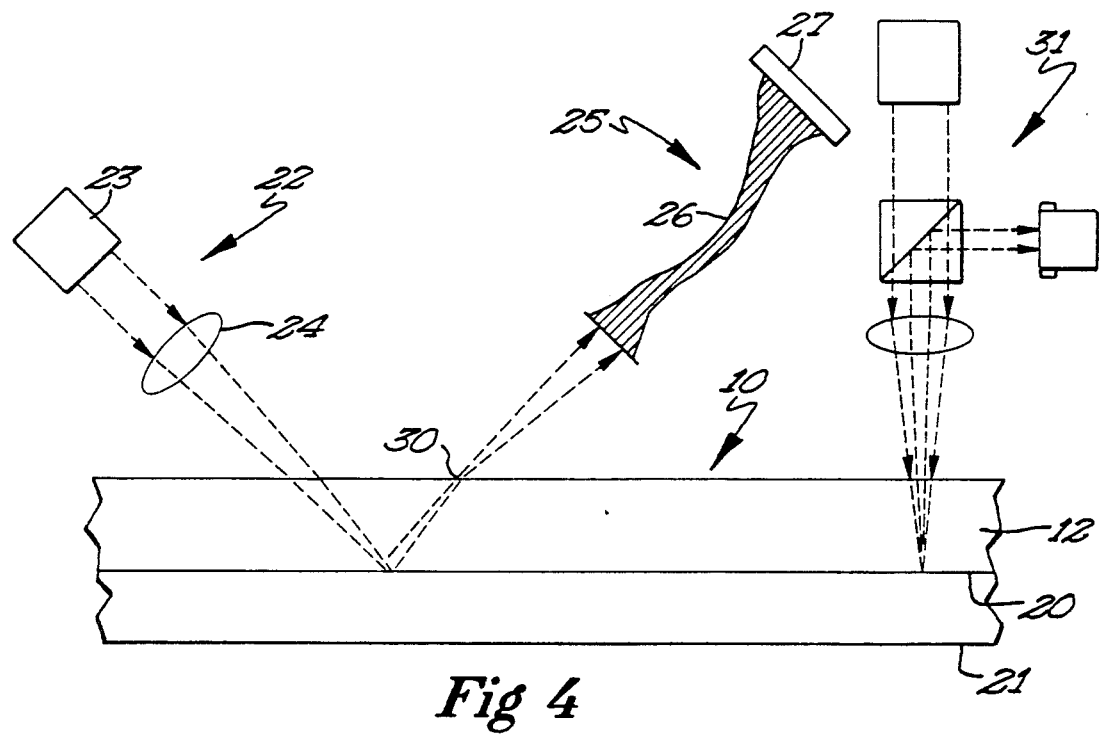
FIG. 4 is a diagrammatic illustration of a preferred embodiment of a portion of the system of the present invention.

Referring now to FIG. 4, there is illustrated an apparatus that may be employed in the practice of the present invention to detect the presence and the amount or concentration of the reactant B' (see FIGS. 1-3) by detecting the number of structures or elements D on the surface of the test strip 12 and, in particular, the number of structures D in each of the standard or control areas and the test area. In the embodiment of FIG. 4, the test strip 12 is provided with a reflective coating at the surface 20 opposite the reaction surface 10. A substrate 21 may be provided for protection of the reflective surface 20 and support of the strip 12, in known manner. A source of laser light is indicated generally at 22 and includes a laser 23 and lens system 24, the lens system 24 focusing the output of the laser 23 onto the reflective surface 20 to converge at the point 30 at the reactive surface 10. A detector unit, designated generally at 25, includes a fiber optic bundle 26 positioned to gather light from the light source 22 (that is reflected by the reflecting surface 20) and a semiconductor array 27. The semiconductor array 27 receives the light gathered by the fiber optic bundle 26 and further includes means for digitizing the pattern of the light images gathered by the fiber optic bundle 26, in known manner.

As is apparent from FIG. 4, an SBC at the point 30 will partially block the light reflected by the surface 20 to result in a shadow in the light gathered by the fiber optic bundle 26. As a result of the divergence of the light beam between the reactive surface 10 and the fiber optic bundle 26, this shadow will be magnified at the entrance to the fiber optic bundle 26 and, accordingly, at the semiconductor array 27. The digitized signal from the array 27 may be interpreted by a processing unit, in known manner. A relative movement between the test strip 12 and a laser/detector assembly (formed of components 22 and 25) will result in a "reading" or scanning of the surface 10 of the strip 12 allowing the SBC to be detected and quantified.

A digital instruction reading unit, designated generally at 31, may be employed to read and interpret data that is prerecorded or encoded on the strip 12. For example, the reflective surface 20 may be provided with nonreflective "holes" which are then read by the reading unit 31 to provide system information and/or calibration data. For example, data may be encoded to identify the strip, the reactants carried on the surface 10 and their location, date of manufacture, expected values at particular test strip locations, etc. Calibration data may be provided to be read during a relative movement between the laser/detector assembly and strip 12 (and the reading unit 31 and strip 12) to provide accurate information as to the speed of that relative motion to assure that the shadow patterns collected by the fiber optic bundle 26 are properly interpreted. Proper focusing of the system elements may also be established and maintained by the digital instruction reading unit 31. Digital instruction reading unit 31 may be of a type known to the prior art. A preferred form of the unit described and shown in the figures is disclosed in Drexler U.S. Pat. No. No. 4,544,835, which is hereby incorporated by reference.

Figure 5:
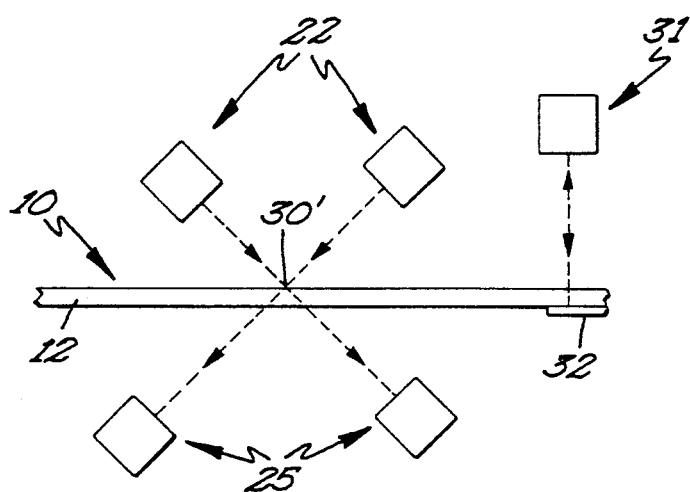
FIG. 5 is a diagrammatic illustration of alternative embodiments to the embodiment of FIG. 4.

In the embodiment of FIG. 4, the strip 12 is provided with a reflective coating 20 with light from the laser source 22 passing to the detector unit 25 through the surface 10 after reflection from the reflective coating 20. A transmittance embodiment is illustrated diagrammatically at FIG. 5 wherein the strip 12 is provided with a reflective coating 32 only for the purposes of the digital instruction reading unit 31 and is otherwise transparent to laser light at locations wherein the surface 10 contains test and control or standard regions. Also, two laser sources 22 and detector units 25 are illustrated. The point of entry 30' of the beams of the laser sources 22 of FIG. 5 corresponds to the point of emergence 30 in the embodiment of FIG. 4 with the sources 22 being focused on the point 30' Each of the light sources 22 and its associated detector unit 25 (as represented by the straight line, dashed beam representations) operate in a manner similar to that described above with reference to the laser source/detector unit of FIG. 4. However, the dual source/detector units of FIG. 5 provide more than a redundancy in that additional data is generated which can be interpreted with greater certainty.

Figure 6:
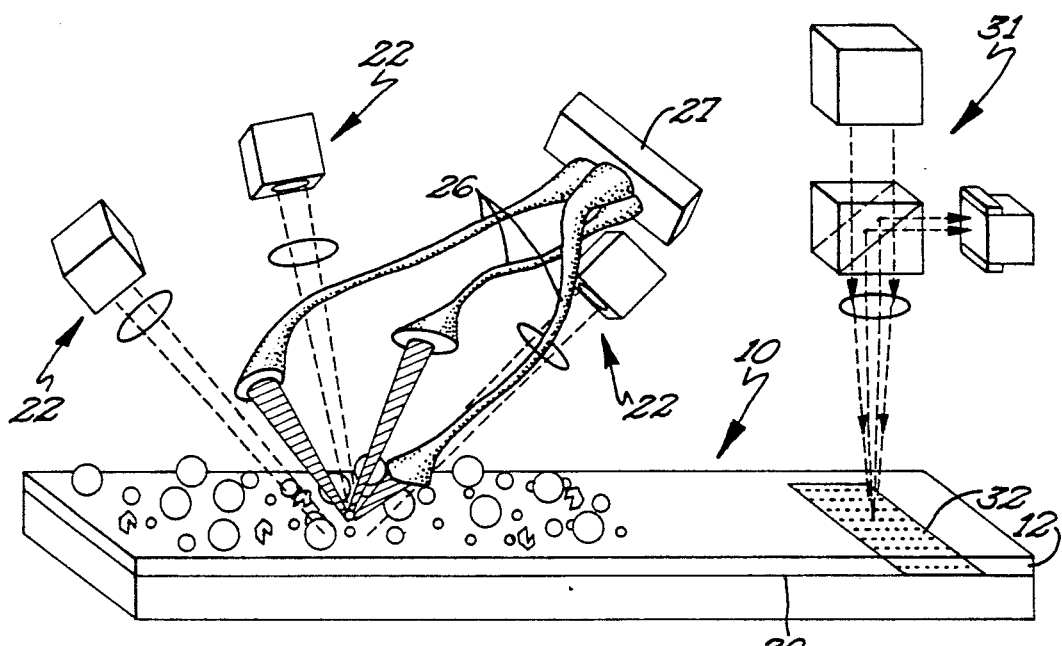
FIG. 6 is a further alternative embodiment in accordance with the system of the present invention.

FIG. 6 illustrates a three beam system in accordance with the present invention with each beam operating in a reflective mode and each beam "arm" being formed by a light source 22 and cooperating fiber optic bundle 26. The fiber optic bundles 26 of the embodiment of FIG. 6 terminate at commonly housed, semiconductor arrays 27 wherein the light patterns gathered by each of the fiber optic bundles 26 are digitized for interrelated interpretation. Again, digital instruction reading unit 31 is provided, and is shown in scanning relation to a region 32 of reflective surface 20, the region 32 of FIG. 6 corresponding directly to the reflective coating 32 of FIG. 5 and containing like data. In the embodiment of FIG. 6, it is anticipated that each of the laser sources 22 will be positioned 120° from each other, as will the fiber optic bundles 26 associated with each laser source 22.

Figure 7:
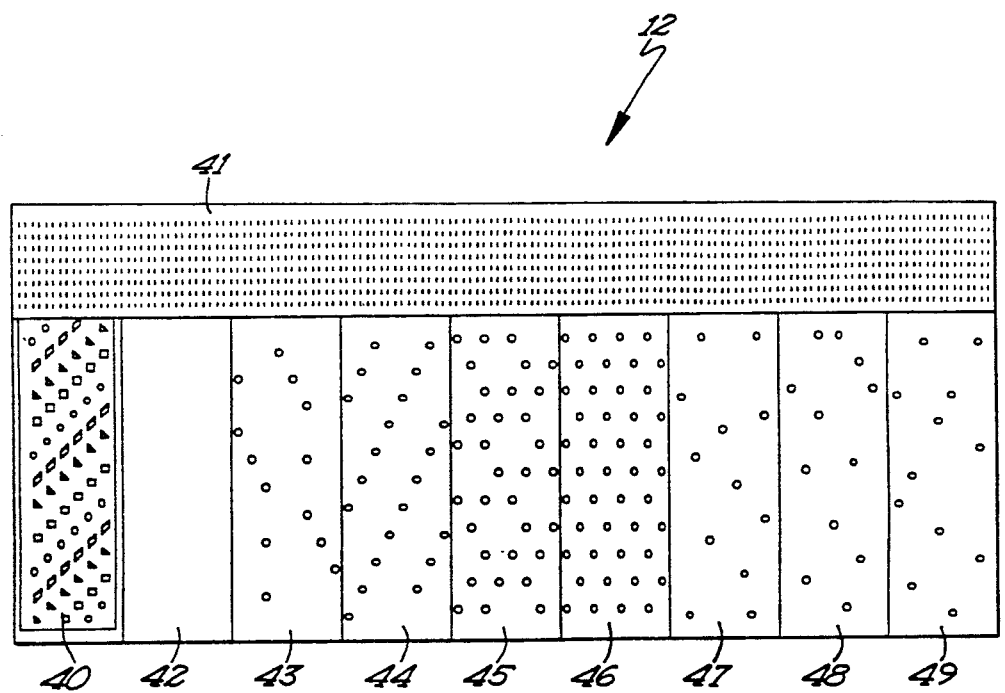
FIG. 7 illustrates a preferred embodiment of a portion of a system in accordance with the present invention.

FIG. 7 illustrates a preferred format for a test strip in accordance with the present invention in the form of a top view of such a test strip having defined regions 40–49. Region 40 contains a calibration pattern which may be scanned in a manner similar to the scan of each of the regions 42–49 to provide focusing and scanning speed data. Region 41 contains digitally encoded instructions which establish the location of the other regions (40 and 42–49) as well as expected or normal values. Other identifying indicia may also be encoded to establish any necessary or desired controls. As described, the region 41 corresponds functionally to the areas 32 shown in FIGS. 5 and 6.

The regions 42–49 may contain the standard and control reagents as well as fixed amounts of the SCR to which the unknown reactant will bind, as described above with reference to FIGS. 1–3. For example, control reagents may be applied to regions 42 and 46 with region 42 being used to determine if any reactants used in the test have a nonspecific affinity for the test strip surface (reactive surface 10; see FIGS. 1–6). Region 46 may contain the maximum number of SBCs possible on the surface of that region. Regions 43–45 may contain known amounts (a dilution series) of a chemical similar to the unknown reactant bound to the SRC. Regions 47–49 may contain fixed amounts of the SRC (a dilution series) to which the unknown reactant will bind. Encoding of regions 40 and 41 may be accomplished in any desired manner consistent with the purposes described herein. Formation of the regions 42–49 may be as described above with reference to FIG. 1. Processing a test strip of the type illustrated in FIG. 7 (in accordance with the description above with reference to FIGS. 2 and 3) will provide a test strip which may be "read" by the apparatus embodiments of FIGS. 4–6, dependent upon the reflective or transmittance characteristics of the particular strip as will be apparent from the description herein.

Figure 8:
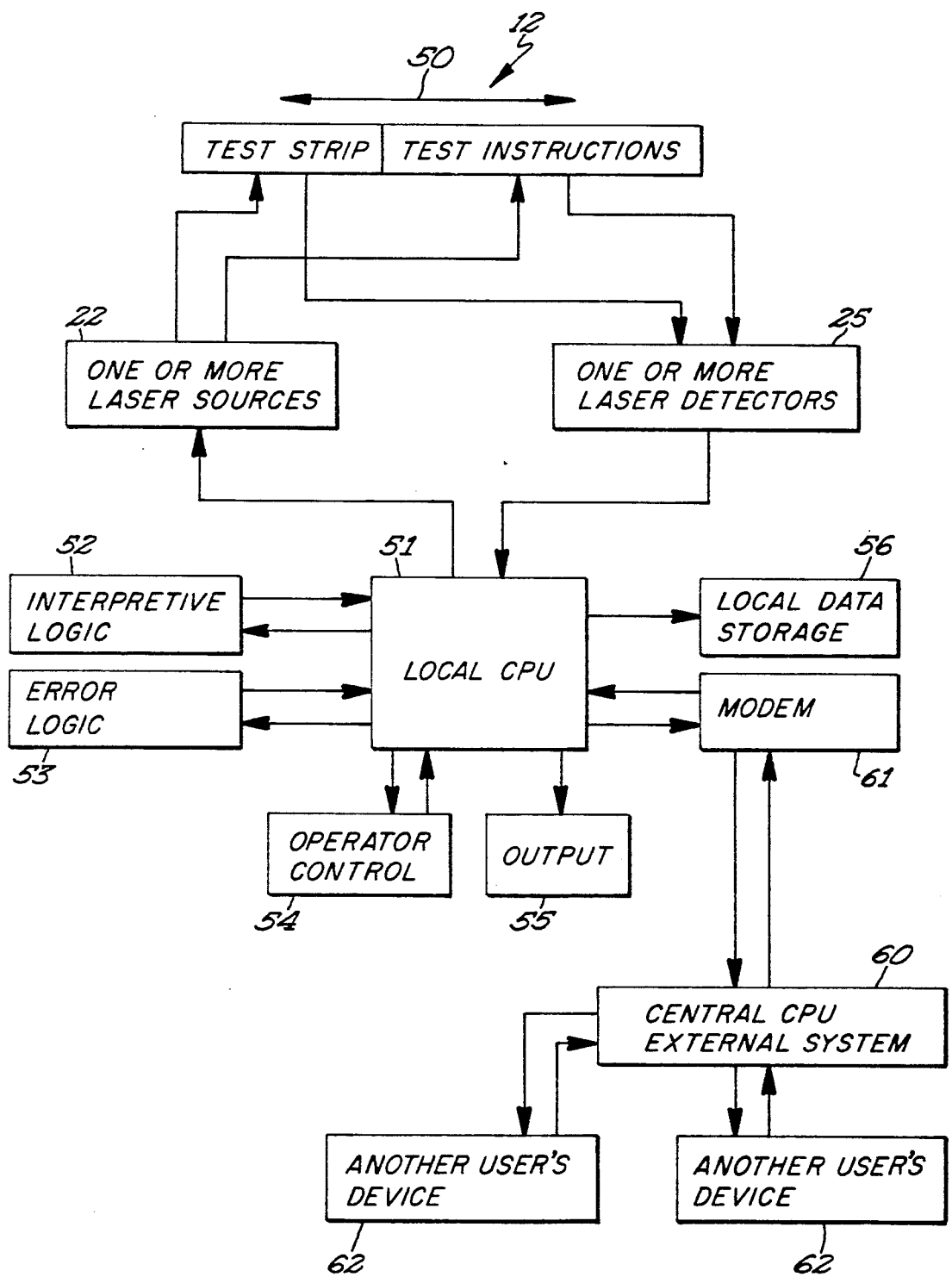
FIG. 8 is a block diagram of a preferred embodiment of a system in accordance with the present invention.

FIG. 8 illustrates a system in accordance with the present invention including a test strip 12, formed and processed as described above, and laser sources 22 and detectors 25. The double headed arrow 50 represents a relative motion between the strip 12 and the laser sources 22 and detectors 25. For the sake of clarity, the digital instruction reading unit 31 is not illustrated specifically, although it may be considered to be contained within the laser source/detector representations of FIG. 8. In any event, data obtained by scanning the digitally encoded instructions contained on the test strip 12 (see Region 41 of FIG. 7) will be loaded into a local CPU 51 for use during processing of the data generated during scanning of the strip regions 42-49. Scanning of the calibration region 40 (see FIG. 7) will establish proper "set-up" and timing information. The data generated on scanning of the regions 42-49, after being digitized as described above, is loaded into the local CPU 51 wherein it is interpreted as represented by the interpretive logic block 52 of FIG. 8. Logic by which the reliability of the data and test procedure is established is represented by box 53 while the operator control and output are represented by boxes 54 and 55, respectively. Calculated data, or raw data, may be maintained in a local storage 56. Accordingly, data read from a test strip 12 will be interpreted, and its reliability established, with any necessary operator control, and an output generated by which an interpretation of the data is provided. That interpretation may include indications for further testing, the results of the test being processed and its significance. The results of that test may be stored for further reference or may be employed to update a data base wherein a historical collection of data is maintained and from which "normal" readings or ranges may be updated as more data and information is gathered. Similar historical and interpretive information may be provided to (and from) a central processing unit 60 via a modem 61, in known manner.

The central processor 60 may be connected to additional devices 62. Each of the devices 62 may correspond directly to the system formed of the components associated with local CPU 51 in FIG. 8. In this manner, each local CPU 51 may be updated by data gathered at the other devices 62 or from information contained within the central CPU 60. Also, operating instructions can be modified and/or updated via the central processor 60 while epidemiologic information can be gathered by the central processor and distributed to the individual devices 62 (including the system specifically described in FIG. 8) with regard to further testing, etc.

Obviously, many modifications and variations of the present invention are possible in light of the above teachings. For example, optical discs are well known in the prior art. A preferred embodiment of the strip 12 of the present invention (in the reflective mode) is formed of a strip of optically transparent material, such as glass, polystyrene, polycarbonate, polyacrylamide or other similar materials. This layer may be approximately 50 microns thick. The substrate 21 (shown in FIGS. 4 and 6) may be of a plastic material having a thickness within the range of 200-400 microns. The digital instruction reading unit 31 may be that disclosed in the incorporated patent, or other comparable device capable of performing in accordance with the teachings herein. As described, this unit provides the focusing functions. However, at least in the embodiments of FIGS. 4 and 6, focusing may be incorporated into the laser sources/detector units. Further, the system of the present invention has been described in the context of a single unknown. It is considered to be within the scope of the present invention to practice its various aspects with a single or with multiple unknown reactants. It is therefore to be understood that, within the scope of the appended claims, the invention may be practiced otherwise unless specifically described.

What is claimed is:

1. A detection system for use during analysis of a specific binding complex, the specific binding complex being carried on a reaction surface of a substrate, the detection system comprising:

a source of analytical radiation;

means directing said analytical radiation through said substrate reaction surface while causing said analytical radiation to converge at said reaction surface;

semiconductor means responsive to the analytical radiation passing through said reaction surface for providing a signal representative thereof; and means for processing said signal.

2. A detection system for use during analysis of a specific binding complex, the specific binding complex being carried on a reaction surface of a substrate, the detection system comprising:

a source of analytical radiation;

means directing said analytical radiation through said substrate reaction surface while causing said analytical radiation to converge at said reaction surface;

means responsive to the analytical radiation passing through said reaction surface for providing a signal representative thereof, said analytical radiation responsive means comprising radiation gathering means and means establishing a pattern representative of gathered radiation wherein said pattern establishing means comprises an array of elements responsive to said analytical radiation; and said analytical radiation responsive elements comprises semiconductor mean; and means for processing said signal.

* * * * *